United States Patent [19]

Lipscomb

[11] Patent Number: 4,720,787
[45] Date of Patent: Jan. 19, 1988

[54] METHODS FOR COAGULATION MONITORING

[75] Inventor: Myatt S. Lipscomb, East Brunswick, N.J.

[73] Assignees: Ortho Diagnostic Systems Inc., Raritan, N.J.; Innovative Medical Systems Corporation, Warminster, Pa.

[21] Appl. No.: 786,925

[22] Filed: Oct. 11, 1985

[30] Foreign Application Priority Data

Oct. 15, 1984 [GB] United Kingdom .................. 8426004

[51] Int. Cl.$^4$ ............................................. G01N 33/86
[52] U.S. Cl. .................................... 364/416; 128/632; 422/73
[58] Field of Search ................ 364/416; 128/632, 637; 422/73; 356/39; 436/69; 435/13

[56] References Cited

U.S. PATENT DOCUMENTS

| | | | |
|---|---|---|---|
| 3,458,287 | 7/1969 | Grose et al. | 436/69 |
| 3,674,012 | 7/1972 | Sage | 128/637 |
| 4,047,890 | 9/1977 | Eichelberger et al. | 364/416 |
| 4,217,107 | 8/1980 | Saito et al. | 436/69 |
| 4,252,536 | 2/1981 | Kishimoto et al. | 422/73 |
| 4,279,616 | 7/1981 | Saito et al. | 422/73 |

*Primary Examiner*—Jerry Smith
*Assistant Examiner*—Kim Thanh Tbui
*Attorney, Agent, or Firm*—Mark A. Hofer; Richard J. Grochala

[57] ABSTRACT

Improved methods for the determination of clotting times of fibrinogen. APTT and PT are provided. Surprising and unexpected accuracy is obtained by combining a backward-looking approach to determine a desired range of values over times T1 and T2, selected in accordance with predetermined percentages of the observed Vmax, thereby avoiding early false positives due to noise and other inhomogeneities from reagent sample mixing. Thereafter, a regression analysis is performed over the time period T1 and T2 and from the derived function, the coagulation time is determined by calculating the time associated with the predetermined percentage of Vmax.

8 Claims, 1 Drawing Figure

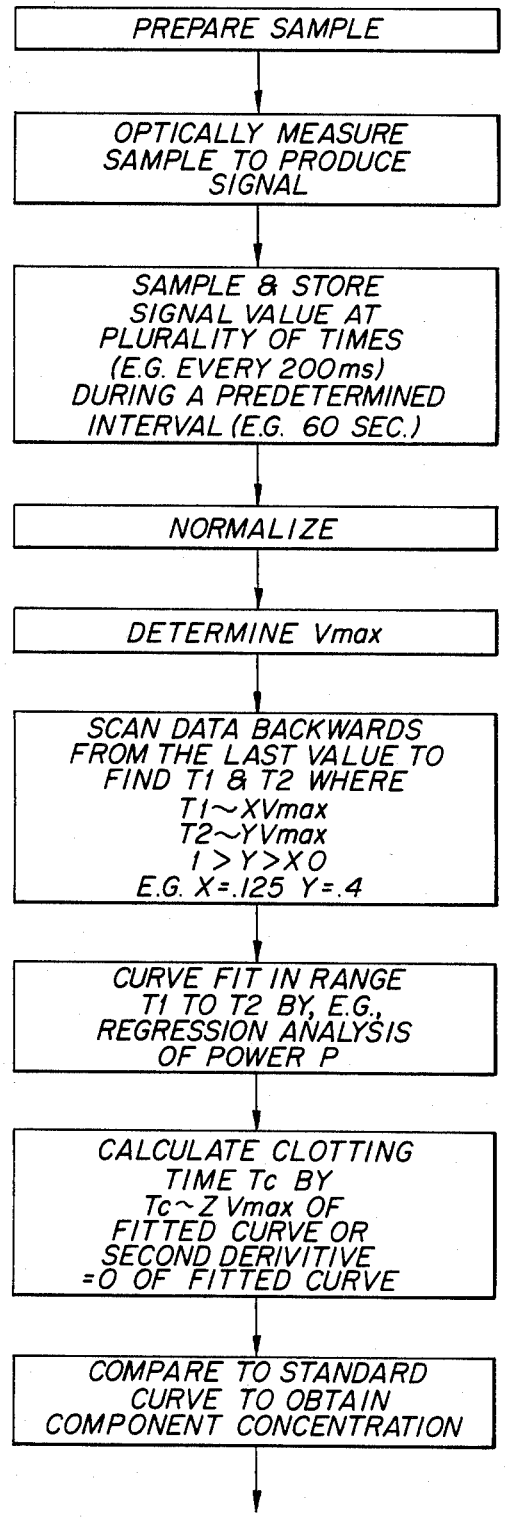

METHODS FOR COAGULATION MONITORING

FIELD OF THE INVENTION

This invention relates to the field of blood coagulation monitoring and more precisely, provides new and improved methods for fibrinogen determination which methods may also be employed in thrombin, partial thromboplastin and prothrombin coagulation tests.

BACKGROUND OF THE INVENTION

Clotting of blood is a complicated process involving a large number of blood components including fibrinogen and prothrombin which is converted to thrombin. It has long been recognized that many aspects of unexplained bleeding or abnormal clotting can be explained in terms of improper levels of these materials in the blood. For instance, states of hypo-fibrinogenemia or hyper-fibrinogenemia may result from hepatic disease, from disseminated intravascular coagulation, from fibrinolytic syndrome, neoplastic disease, and post-operatively due to trauma. By monitoring the fibrinogen, thrombin and prothrombin levels within the blood, a physician may acquire meaningful data concerning the patient's blood clotting abilities. For example, the Activated Partial Thromboplastin Time (APTT) Test measures coagulation factors of the intrinsic pathway. These factors include Factors XII, XI, IX, VIII, X, V, II and I which may be abnormal based on heredity or heparin therapy. Thus, the APTT test is useful as a presurgical screen and for monitoring heparin therapy. Similarly, fibrinogen testing (by the Thrombin Time (TT) test or quantitative fibrinogen test) provides useful diagnostic data when unexplained bleeding or abnormal clotting occurs.

As a result, substantial efforts have been made to measure these clotting components, particularly that of fibrinogen, the most difficult of these to measure accurately. Most methodologies rely upon immunologic and clotting techniques although clearly the latter is preferred. The immunologic techniques, although generally capable of precisely defining the levels of the various components within the blood stream, are incapable of distinguishing between active and inactive forms. Accordingly, the immunologic methods are felt to be less accurate with respect to the patient's actual clotting ability.

Consequently, the results obtained by clotting techniques are preferred as being more clinically significant. Most of these methods rely upon the addition of excess thrombin to dilute plasma and the measurement of the resultant clotting time is then related to the fibrinogen concentration of the plasma. This is the original fibrinogen assay described by Clauss in Gerinnungsphysiologische Schelimethode Zur Bestimung Des Fibrigens, ACTA Haemat 17:237–246 (1957).

Another useful reference regarding the processes and components involved in blood coagulation and methods for monitoring such coagulation are disclosed in "Hemostatsis and Thrombosis, A Conceptual Approach", Churchill, Livington, U.S. 1979.

Typically, most instruments detect the formation of a clot by monitoring either optical turbidity or electrical conductivity. The latter represents the traditional approach employed by the so-called fibrometer-type of instrument. Effectively, this instrument measures increasing conductivity which may be correlated to the formation of clots. Similarly, turbidity may be optically sensed by the decrease in light transmission due to the formation of a clot. Certainly with the normal PT or APTT tests, these methods have found widespread acceptance despite the fact that each test has associated therewith a level of indefiniteness regarding the point at which the clot is determined to have occurred. Inasmuch as the fibrometer represents the traditional approach, and most physicians and clinicians are accustomed to utilizing this approach, as a practical matter all other instruments, to be accepted, should have a high degree of correlation with the fibrometer.

It is one aspect of the present invention to provide improved methods especially useful with optical clot detection techniques which have a high level of correlation with the standard fibrometer.

Detection of fibrinogen levels has historically been the most difficult of the tests to perform particularly with hypo-fibrinogenemic samples. This occurs because the formation of the clot is a lengthy process subject to substantial error in the determination of when that clot has formed. Substantial problems are incurred with the need to discriminate between true clot formation and aberrant signal noise accruing as a result of reagent mixing, and the passage of air bubbles or other nonrelevant particulate matter in front of the optical sensors. Often, these noise producers may be erroneously interpreted by the instrument as early clots and a false early clot detection displayed. This occurs as a result of the enormous difficulty associated with determining what incoming data represents a clot as opposed to aberrant noise. This problem is characteristic of the forward looking approach characteristic of conventional instruments which analyze data as it is accumulated.

It is an object of the present invention to provide new and improved methods useful for fibrinogen and quantitative fibrinogen detection.

It is a related object to provide methods which may be used for other coagulation monitoring including PT and APTT.

It is yet another aspect of the present invention to provide methods useful for optical clot detection. These and other objects and aspects of the present invention will become clear upon study of the ensueing detailed description.

SUMMARY OF THE INVENTION

In accordance with the principles and aspects of the present invention, new and improved methods for coagulation monitoring are provided and involve the combined use of two departures from conventional approaches. The first departure involves analyzing the data only after it has been fully accumulated by utilizing a "backwards looking" approach. This approach provides, as one advantage, the capacity to avoid false early clotting detection times which would otherwise result from detecting air bubbles from reagent mixing and other such errors characteristic of prior techniques. Secondly, the methods of the present invention require the performance of curve smoothing techniques over a selected range of the data points whereby desired clotting times may be calculated on the basis of a predetermined percentage of a maximally derived sensor signal utilizing the derived, smoothed curve analysis. Preferably, the curve smoothing will involve a regression analysis, most preferably of a linear and polynomial nature.

Thereafter, the computed coagulation times may be, if desired, conventionally referenced to a standard curve to obtain the applicable component's concentration within the sample. In a most preferred embodiment of the present invention, the raw sensor data is normalized subsequent to collection and prior to initiating any calculations to thereby simplify and enhance the accuracy of the curve fitting technique employed.

BRIEF DESCRIPTION OF THE DRAWING

The drawing is a flow chart of the method according to the present invention.

DETAILED DESCRIPTION OF THE INVENTION

The methods of the instant invention are intended for use with conventional coagulation reagents and optical clot detecting instruments of standard configuration. These instruments traditionally analyze data as it is being accumulated in order to detect clots as they initiate. As previously indicated, such methods encounter difficulties with unusually turbid samples, e.g. lipemic samples with very weak signals containing a low signal to noise ratio, with inconsistencies in reagent mixing for producing air bubbles and the like artifacts all of which yield false early results.

The methods of the present invention avoid these limitations characteristic of prior art methods by first accumulating all of the data over a predetermined interval set to encompass all possible samples whether whole or diluted. With optical detection sensors, this data is generally available on a continuous basis and may then be suitably inputted into an analog to digital converter for subsequent digital storage and manipulation. Although the use of continuous data would be most preferred, hardware limitations with respect to data storage, computing power, and throughput time goals dictate more practical constraints. Accordingly, a convenient compromise provides for sampling the data stream on a consistent basis for example, every 200 milliseconds for 60 seconds after the end of the blank time (that time necessary to adjust the instrument to accomodate the sample's turbidity and to effect mixing of reagents). Such a sampling rate results in 300 data points, a number large enough to ensure accuracy but small enough to be readily handled by suitably programmed central processing units (CPUs), i.e. preferably an INTEL 8088 or equivalent, of modest size which are commercially available at reasonable cost. During their accumulation, these data points are stored in a memory location where they may be subsequently obtained for further manipulation. The data points typically are optical detector voltages which correlate with the degree of sample turbity or transmissibility, a function of clotting. They are stored in combination with their respective time of collection.

The most preferred mode of the present invention will then normalize the voltage versus time data by scanning the data for the minimum voltage occurrence. This minimum voltage then becomes the zero voltage and all other voltages are adjusted accordingly to result in a normalized voltage versus time curve to a base line of zero volts.

Thereafter, the maximum voltage (Vmax) is preferably by averaging the last five data points. The actual number averaged may be altered as preferred or dispensed with altogether in preference of the last accumulated value, assumed to be Vmax. The disadvantage with the latter method is the possible use of a data point less representative of the maximum voltage due to a sample or reading inhomogeneity which introduces inadvertent error. It will be intuitively clear that averaging a few data points at the end of the collection time should serve to substantially reduce or eliminate any such possible error.

In a radical departure from prior methods, the values are then scanned backwards starting with the last acquired voltage (i.e. towards the first acquired or normalized value), to determine the occurrence of two particular voltages whose associated times will be designated T1 and T2. The T1 and T2 voltages are determined on the basis of predetermined percentages of the maximum voltage. For example, these percentages may be on the order of 12.5% of the average maximum voltage for time T1 and 40% of the average maximum voltage for time T2. The choice of these percentages will be experimentally predetermined based upon the type of clotting tests to be performed, and the type of subsequent smoothing analysis to be rendered upon the data for determining the clotting time. Additional discussion regarding the manner of selecting appropriate percentages will be presented later suffice it to say for the moment that the data over the T1 to T2 range is presumed to be the most accurate.

In one embodiment of the present invention, a straightline regression analysis is then performed over the data from time T1 to time T2 in order to derive an equation which best fits the data. This procedure effectively smoothes the data further eliminating unintentional error and data inhomogeneities which can have a variety of sources. The particular clotting time is then calculated from the linear regression analysis for the time when the voltage reaches a certain, predetermined percentage of the maximum voltage. This predetermined percentage is also experimentally determined by comparison of the instruments results with fibrometer-type tests. Typically, it may be on the order of 40% of the maximum voltage.

A most preferred embodiment will further allow the computed coagulation time, e.g. thrombin time etc., to be referenced in a convenient manner to a standard curve derived from previously performed known samples to obtain the fibrinogen concentration or other clotting component of the patient sample. Such referencing to a standard will, of course, take into account such things as sample dilution and the like. Comparison to standard curves is a process which is readily understood by those skilled in the art.

The foregoing methods are preferably incorporated into software which can be performed on economical and readily available CPUs with convenient dispatch. Most preferred embodiments will further include various checks within the software to ensure that valuable data is derived. For instance, these checks could include substantiation that the number of regression data points is greater than 3, that there is an overall positive slope to the calculated regression line, that the maximum voltage change exceeds a minimum threshold and that the regression correlation coefficient and residual means square (as a CV percent) are within experimentally determined allowable limits.

Another preferred embodiment of the foregoing involves scanning the normalized voltages for the first occurrence of a voltage less than or equal to 0.975 times the average maximum voltage (time 2) and $\leq 0.025$ times the average maximum voltage change for time 1. This approach extends the range of T1 to T2 from $2\frac{1}{2}\%$ to $97\frac{1}{2}\%$ of Vmax.

Thereafter, a polynomial regression analysis of higher order, say third or fourth order (as opposed to first order for the 12½ to 40% range), is performed and the clotting time (e.g. thrombin) calculated from that derived function as the time that the voltage function reaches 0.4 times the maximum voltage. One way of calculating the thrombin time (when a polynomial order greater than 1 is used) is by an iterative binary search process (also known as a bisection algorithm) whereby the time variable (X) is varied until the polynomial functions returns a Y value (voltage) within a very close percentage (about 0.0001%) of 40% of Vmax.

The foregoing has been described in terms of fibrinogen assays, however, the methods are equally applicable to thromboplastin (PT) or activated partial thromboplastin (APTT) assays. These are performed by adding brain thromboplastin or activated partial thromboplastin respectively, to a plasma sample and determining the time at which the clot forms. Reagents useful for these purposes include for instance Ortho Quantitative Fibrinogen Assay (Q.F.A.). Ortho Q.F.A. Thrombin (Human), Ortho Q.F.A. Buffer, Ortho Activated PTT Reagent, Ortho Activated Thrombofax ™ Reagent, Ortho Brain Thromboplastin, Fibrindex ™ Thrombin, Ortho Plasma Coagulation Controls (obtainable from Ortho Diagnostic Systems Inc., Raritan, N.J. These materials, standard in the industry, are accompanied by procedural instructions regarding their use, the relevant portions of which are incorporated herein by reference. Either of the two generalized embodiments of the methods of the present invention may be utilized for calculating PT or APTT coagulation times.

Still another embodiment useful for calculating detecting clots includes obtaining from the normalized data T2 and T1 in accordance with 0.975 and 0.025 times the maximum voltage (Vmax). This provides a significantly greater range of the collected data. Thereafter a polynomial regression analysis of order P is performed on the voltage versus time data over the time interval T1 to T2. The order P is preferably determined experimentally in accordance with the capability of the sensor-instrument and the ability to produce fibrometer-type values within a reasonable period of time. Although increasing order P is accompanied by more precise curve fitting, the calculation time and hardware required to perform such calculations greatly increases beyond that reasonably necessary.

The fitted curve parameters describe/predict a calculated voltage in place of the actual or observed voltage for each time T, thereby producing a smoothened signal substantially devoid of noise. This method may be expected to predict a curve which approximates a sigmoid. The smoothed curve may then be differentiated twice producing parameters describing a curve of order P-2. From this derived curve, the estimated voltages represent second derivative estimates. By identifying the time (T) when the second derivative is zero, corresponding to the inflection point of the original curve, one may identify the coagulation component (e.g. APTT or PT) time. If P2 is greater than 1, T may also be computed by an iterative binary search process whereby T is varied until the polynomial solution returns a Y value substantially equal to zero or by any suitable root-finding algorithm. On the other hand, if the regression analysis of the smooth differentiated curve is linear (P=1) then T may be computed as minus B0/B1 where B0 and B1 are the Y intercept and the slope of the first order second derivative, respectively.

OPTIMIZATION PROCEDURES

A significant advantage accompanying the novel methods of the instant invention is the ability to tailor the methods in accordance with the instruments sensitivity, the CPU and memory capacity, the accuracy desired and the throughput required. The tailoring of the methods is not difficult and may be readily performed by one skilled in the art in accordance with the following optimization procedures.

The length of time that data is obtained, for example 60 seconds in the fibrinogen assay, is chosen as a compromise between the time needed for the clotting reaction to reach near completion and the achievement of a reasonable test throughput for the instrument. For PT and APTT assays, the length of time chosen is preferably the selected maximum endpoint for a given instrument/test situation. The number of data points collected, preferably on the order of 300 in the fibrinogen assay methods described above, is advantageously selected giving due consideration to memory-hardware limitations and to the CPU time required to perform the methods of the instant invention. Too few data points, such as 25 for example, would not accurately represent the time analog curve while too many data points could result in an inordinant amount of process time unless excessive CPU and memory capacity is employed. The speed of calculation can be augmented by reducing the complexity of the necessary calculations through a normalization process. The normalization process is performed by searching for a minimum occurring voltage and subtracting that minimum voltage from all other data points. Preferably, greater speed may be obtained by programming the CPU to "remember" the minimum voltage occurrence as data is collected during the 60 seconds thereby eliminating this as a separate step. The resultant data points are then normalized with respect to the minimum voltage, set to zero.

As previously described, Vmax is preferably identified as an average of a limited number of the final data points collected. Too large an average will reduce the value of Vmax while too small an average insufficiently vitiates a possible erroneous value.

The percentage of the maximum voltage which is used to identify time, T1, and time, T2, in the reaction, for example "0.4 times the average maximum voltage change and 0.125 times the average maximum voltage change" in the fibrinogen examples, are not critical. These values were chosen on the basis of the type of curve fit to be subsequently performed. In the described method for the fibrinogen test reaction, the curve interval between 12.5% and 40% of the maximum voltage change approximates a straight line thereby allowing for a linear, first order (P=1) polynomial regression analysis. Similarly, if a higher order regression analysis is performed, for example a fourth order, then the area of analysis can be broadened to say an interval of 2½% to 97½% of Vmax.

The clotting time calculated from the derived function is preferably chosen to closely match the clotting times reported by existing instrumentation in the coagulation laboratory. Such times are preferred since they have been substantially accepted by clinicians. Accordingly, it may be expected that clotting times with substantial variation therefrom will not only face difficult acceptance, but will result in ultimate confusion regarding their meaning. For instance, the time reported at 0.4 times (e.g. 40%) of the maximum voltage is quite comparable to fibrinogen times reported by the BBL Fibrometer, an instrument of more traditional design. For the PT or APTT determinations, a calculation at 0.05 or 0.1 times the maximum voltage is generally more appropriate and preferred.

Still other optimization procedures may be instituted and include the performance of a linear transformation prior to a linear regression analysis in order to effect a better curve fit. Linear, as used throughout, is intended to mean that the final approximation function is linear in its parameters, in other words, f(t) is a sum of terms involving powers of t.

Although one may "pick" clotting time end points by either determining when the derived regression analysis curve reaches an arbitrary percentage of maximum optical density change (e.g. voltage) or, the point in time when the second derivative of the approximation function is equal to zero, it will be understood that significantly better replicate precision is obtained by the former method. In most applications it is thus preferred over the latter.

Following optimization, the methods of the instant invention will provide increased sensitivity regarding the detection of clotting times due in large measure to the reduction of noise effects in the clotting time. Further, the inventive methods provide statistically valid data which may be used to set confidence levels on the final clotting time results. This latter point is an especially important advantage in that it permits singlet sample testing as opposed to the heretofore required double sample testing. Reducing the requisite sample numbers in half reduces concomitant reagent and personnel resource expenditures, especially critical in the financially constrained clinical environment, as well as increasing throughput capacity.

Lastly, instead of a polynomial regression analysis, one can substitute, therefore, a cubic spline fit which is commonly understood to mean reiterative curve fitting over small sections in order to formulate a table of coefficients thereby allowing subsequent interpolation between coefficients when solving for X or Y. For purposes of calculating a clotting time, the use of a cubic spline fit shall be deemed an equivalent to polynomial regression analysis. The cubic spline is less preferred as no validating static data can be easily obtained.

These and other principles of the instant invention will be demonstrated by the following Examples.

EXAMPLE 1

A fibrinogen assay was performed on a Koagulab 40A ™ (available from Ortho Diagnositic Systems Inc., Raritan, N.J.) and the data analyzed on an Apple II computer. 300 data points were collected and the reaction curve (optical sensor voltage versus time) was evaluated by the backward-looking approach of the instant invention. An interval of 25% to 50% of the maximum voltage change (average of last five voltage values) was located and fitted with a first order polynomial. The slope parameter was correlated with fibrinogen concentration along with the time at which 25% of Vmax occurred.

Three vials of Ortho Plasma Coagulation Control (OPCC) 337 (252 mg/dl, obtainable from Ortho Diagnostic Systems Inc., Raritan, N.J. was pooled. Six vials of Thrombin QFT04 was pooled. The following OPCC dilutions were prepared:

| Dilution | Volume OPCC | Volume of QFA Buffer |
|---|---|---|
| 1/5 | 0.8 ml | 3.2 ml |
| 1/15 | 0.3 ml | 4.2 ml |
| 1/40 | 0.1 ml | 3.9 ml |

0.2 ml of the 1/5 dilution was pipetted into curvette positions 1–3 for both channels. The Koagulab was run in the manual fibrinogen assay. Data was collected by the Apple II computer every 0.2 seconds for 60 seconds and stored on a magnetic disk. A second run was done in the same way for the 1/15 dilutions and a third one with the 1/40 dilutions. Analog output was recorded on a chart recorder for channel 2. Runs 4–6 were done in the same manner as runs 1–3, except the chart recorder was on channel 1. The following results were obtained:

| | Slope Method | | | |
|---|---|---|---|---|
| Dilution | Fibrinogen mg/dl | Variance mg/dl$^2$ | df | cv |
| 1/5 | 504 | 230.2 | 8 | 3.01% |
| 1/15 | 181 | 27.54 | 8 | 2.90% |
| 1/40 | 68 | 37.92 | 8 | 9.06% |

| | Start Time Method | | | |
|---|---|---|---|---|
| Dilution | Fibrinogen mg/dl | Variance mg/dl$^2$ | df | cv |
| 1/5 | 510 | 203.0 | 8 | 8.83% |
| 1/15 | 164 | 53.3 | 8 | 4.45% |
| 1/40 | 63 | 7.69 | 8 | 4.40% |

EXAMPLE 2

The foregoing Example was repeated except that the end point or thrombin time was computed after regression analysis over a 12.5% to 40% delta voltage range. The clotting end point was specifically calculated as $X = [(0.4\ V_{max}) - \text{intercept}]/\text{slope}$. The following results were obtained:

| Assay 279 mg/dl | Assay 100 mg/dl | Assay 60 mg/dl |
|---|---|---|
| 278 | 95 | 62 |
| 260 | 88 | 60 |
| 268 | 89 | 57 |
| 260 | 85 | 57 |
| 278 | 95 | 62 |
| 288 | 88 | 57 |
| 268 | 91 | 62 |
| 260 | 91 | 62 |
| 260 | 94 | 62 |
| 268 | 94 | 63 |
| 268 | 86 | 60 |
| 260 | 91 | 62 |
| 278 | 93 | 64 |
| 252 | 91 | 66 |
| 268 | 77 | 64 |
| 260 | 91 | 66 |
| Avg. = 267 mg/dl | Avg. = 89 mg/dl | Avg. = 61 mg/dl |
| C.V. = 3.56% | C.V. = 5.10% | C.V. = 4.49% |

EXAMPLE 3

Frozen patient samples were obtained from three hospital locations for testing a Koagulab 40A instrument utilizing the methods of the present invention in comparison with a Fibrometer reference instrument.

Standard OPCC dilution curves were run each day on both instruments. Patient specimens were prediluted according to the published Ortho QFA protocol. Generally this included dilution 1–5 of specimens with a reported fibrinogen of less than 55 mg/dl while specimens greater than about 550 mg/dl were diluted 1–20 or 1–30 into QFA buffer. Standards in patient samples were tested concurrently on the Koagulab 40A and Fibrometer in random order. Sample fibrinogen results were determined by referencing the sample thrombin time to the standard curve. From the results it was determined the mean Koagulab 40A replicate precision was 4.7% (34 df). The mean fibrometer precision was 3.0%. The precision of each instrument was estimated as the square root of the sum of C.V.$^2$/n where C.V. was the replicate specimen precision and n was 34 and 29 for the Koagulab 40A and fibrometer respectively. The mean delta between instrument type across patient specimens was 13.2 mg/dl. Half of this difference was accounted for by two patients and if these are excluded, the mean delta average becomes 6.2 mg/dl. As indicated by the following data, the Koagulab 40A results correlates strongly with the fibrometer reference.

TABLE 1

KOAGULAB 40A and FIBROMETER COMPARISON PATIENT DATA

| PATIENT ID | | CH 1 mg/dl | CH 2 mg/dl | AVG mg/dl | CV % | REP 1 mg/dl | REP 2 mg/dl | 2 AVG mg/dl | CV % | DELTA AVG |
|---|---|---|---|---|---|---|---|---|---|---|
| | | KOAGULAB 011 DAY 1 | | | | FIBROMETER 21579 DAY 1 | | | | |
| blackwell | 1:05 | 40 | 44 | 42 | 6.733 | 34 | 33 | 33 | 2.142 | 9 |
| blackwell | 1:10 | 54 | 49 | 51.5 | 6.864 | — | — | — | — | — |
| doxsey | 1:05 | 20 | 19 | 19.5 | 3.625 | 14 | 14 | 14 | 0 | 5.5 |
| | | KOAGULAB 011 DAY 2 | | | | FIBROMETER 21579 DAY 2 | | | | |
| patient a | 1:10 | 163 | 158 | 160.5 | 2.202 | 174 | 166 | 170 | 3.327 | −9.5 |
| patient b | 1:10 | 111 | 118 | 114.5 | 4.322 | 113 | 117 | 115 | 2.459 | −0.5 |
| patient c | 1:20 | 753 | 764 | 758.5 | 1.025 | 796 | — | 796 | — | −37.5 |
| patient d | 1:10 | 727 | 734 | 730.5 | 0.677 | 710 | 710 | 710 | 0 | 20.5 |
| patient e | 1:10 | 198 | 203 | 200.5 | 1.763 | 193 | 193 | 193 | 0 | 7.5 |
| patient f | 1:10 | 513 | 517 | 515 | 0.549 | 456 | 456 | 456 | 0 | 59 |
| patient g | 1:20 | 510 | 529 | 519.5 | 2.585 | 525 | 525 | 525 | 0 | −5.5 |
| patient h | 1:10 | 166 | 174 | 170 | 3.327 | 183 | — | 183 | — | −13 |
| patient i | 1:10 | 671 | 725 | 698 | 5.469 | 518 | 599 | 558.5 | 10.25 | 139.5 |
| patient j | 1:10 | 114 | 117 | 115.5 | 1.836 | 121 | 121 | 121 | 0 | −5.5 |
| patient k | 1:20 | 351 | 236 | 293.5 | 27.70 | 496 | 306 | 401 | 33.49 | −107. |
| patient l | 1:10 | 474 | 487 | 480.5 | 1.913 | 456 | 456 | 456 | 0 | 24.5 |
| patient m | 1:20 | 578 | 598 | 588 | 2.404 | 565 | 565 | 565 | 0 | 23 |
| patient n | 1:20 | 643 | 664 | 633.5 | 2.270 | 656 | 656 | 656 | 0 | −2.5 |
| casper | 1:10 | 46 | 45 | 45.5 | 1.553 | 48 | — | 48 | — | −2.5 |
| casper | 1:05 | 34 | 36 | 35 | 4.04 | 35 | 33 | 34 | 4.158 | 1 |
| hernan | 1:20 | 807 | 882 | 844.5 | 6.279 | 734 | 734 | 734 | 0 | 110.5 |
| | | KOAGULAB 016 DAY 3 | | | | FIBROMETER 21579 DAY 3 | | | | |
| patient s | 1:10 | 53 | 59 | 56 | 7.575 | 26 | 27 | 26.5 | 2.667 | 29.5 |
| patient x | 1:10 | 197 | 195 | 196 | 0.721 | 176 | 186 | 181 | 3.906 | 15 |
| hollenbec | 1:10 | 65 | 59 | 62 | 6.841 | 63 | 63 | 63 | 0 | −1 |
| speight | 1:10 | 126 | 122 | 124 | 2.280 | 119 | 115 | 117 | 2.417 | 7 |
| patient t | 1:10 | 216 | 206 | 211 | 3.351 | 186 | 186 | 186 | 0 | 25 |
| patient u | 1:10 | 199 | 189 | 194 | 3.644 | 186 | 176 | 181 | 3.906 | 13 |
| patient p | 1:10 | 60 | 58 | 59 | 2.396 | 49 | 48 | 48.5 | 1.457 | 10.5 |
| smith | 1:10 | 155 | 150 | 152.5 | 2.318 | 136 | 134 | 135 | 1.047 | 17.5 |
| patient o | 1:10 | 63 | 55 | 59 | 9.586 | 52 | — | 52 | — | 7 |
| patient z | 1:30 | 1173 | 1138 | 1155. | 2.141 | 1285 | 1199 | 1242 | 4.896 | −87 |
| patient q | 1:10 | 104 | 98 | 101 | 4.2 | 92 | — | 92 | — | 9 |
| patient w | 1:10 | 200 | 192 | 196 | 2.885 | 186 | 197 | 191.5 | 4.061 | 4.5 |
| gormley | 1:05 | 48 | 42 | 45 | 9.426 | 43 | 43 | 43 | 0 | 2 |
| patient v | 1:10 | 233 | 208 | 220.5 | 8.013 | 209 | 197 | 203 | 4.179 | 17.5 |
| patient r | 1:10 | 112 | 99 | 105.5 | 8.712 | 101 | 104 | 102.5 | 2.069 | 3 |
| patient y | 1:20 | 938 | 964 | 951 | 1.932 | 899 | 899 | 899 | 0 | 52 |

EXAMPLE 4

The data from Example 3 was reanalyzed on an external computer utilizing a fourth order polynomial regression analysis over a range of 2.5 to 97.5% of maximum voltage. These results are compared to the original fibrinogen data obtained from the first order regression analysis performed in Example 3. The following data was obtained:

TABLE 2

FIBRINOGEN ALGORITHM COMPARISON PATIENT DATA

| PATIENT ID | | POLYNOMIAL | | | | STRAIGHT LINE | | | | DELTA AVG |
|---|---|---|---|---|---|---|---|---|---|---|
| | | CH 1 mg/dl | CH 2 mg/dl | AVG mg/dl | CV % | CH 1 mg/dl | CH 2 mg/dl | AVG mg/dl | CV % | |
| blackwell | 1:10 | 54 | 51 | 52.5 | 4.04 | 54 | 49 | 51.5 | 6.86 | 1˙ |
| doxsey | 1:05 | 21 | 20 | 20.5 | 3.44 | 20 | 19 | 19.5 | 3.62 | 1 |
| blackwell | 1:05 | 40 | 43 | 41.5 | 5.11 | 40 | 44 | 42 | 6.73 | −0.5 |
| patient e | 1:10 | 204 | 209 | 206.5 | 1.71 | 198 | 203 | 200.5 | 1.76 | 6 |
| patient j | 1:10 | 112 | 115 | 113.5 | 1.86 | 114 | 117 | 115.5 | 1.83 | −2 |

TABLE 2-continued
FIBRINOGEN ALGORITHM COMPARISON
PATIENT DATA

| | | POLYNOMIAL | | | | STRAIGHT LINE | | | | |
|---|---|---|---|---|---|---|---|---|---|---|
| PATIENT ID | | CH 1 mg/dl | CH 2 mg/dl | AVG mg/dl | CV % | CH 1 mg/dl | CH 2 mg/dl | AVG mg/dl | CV % | DELTA AVG |
| patient n | 1:20 | 670 | 690 | 680 | 2.07 | 643 | 664 | 653.5 | 2.27 | 26.5 |
| patient c | 1:20 | 770 | 792 | 781 | 1.99 | 753 | 764 | 758.5 | 1.02 | 22.5 |
| patient m | 1:20 | 598 | 622 | 610 | 2.78 | 578 | 598 | 588 | 2.40 | 22 |
| patient g | 1:20 | 528 | 542 | 535 | 1.85 | 510 | 529 | 519.5 | 2.58 | 15.5 |
| patient l | 1:10 | 496 | 498 | 497 | 0.28 | 474 | 487 | 480.5 | 1.91 | 16.5 |
| patient h | 1:10 | 169 | 178 | 173.5 | 3.66 | 166 | 174 | 170 | 3.32 | 3.5 |
| patient i | 1:10 | 701 | 751 | 726 | 4.86 | 671 | 725 | 698 | 5.47 | 28 |
| hernon | 1:20 | 846 | 912 | 879 | 5.30 | 807 | 882 | 844.5 | 6.27 | 34.5 |
| patient b | 1:10 | 111 | 119 | 115 | 4.91 | 111 | 118 | 114.5 | 4.32 | 0.5 |
| patient d | 1:10 | 791 | 788 | 789.5 | 0.26 | 727 | 734 | 730.5 | 0.67 | 59 |
| patient a | 1:10 | 166 | 158 | 162 | 3.49 | 163 | 158 | 160.5 | 2.20 | 1.5 |
| patient f | 1:10 | 547 | 543 | 545 | 0.51 | 513 | 517 | 515 | 0.54 | 30 |
| casper | 1:10 | 48 | 45 | 46.5 | 4.56 | 46 | 45 | 45.5 | 1.55 | 1 |
| casper | 1:05 | 34 | 35 | 34.5 | 2.04 | 34 | 36 | 35 | 4.04 | −0.5 |
| patient s | 1:10 | 53 | 59 | 56 | 7.57 | 53 | 59 | 56 | 7.57 | 0 |
| patient x | 1:10 | 202 | 198 | 200 | 1.41 | 197 | 195 | 196 | 0.72 | 4 |
| hollenbec | 1:10 | 64 | 59 | 61.5 | 5.74 | 65 | 59 | 62 | 6.84 | −0.5 |
| speight | 1:10 | 127 | 122 | 124.5 | 2.83 | 126 | 122 | 124 | 2.28 | 0.5 |
| patient t | 1:10 | 224 | 211 | 217.5 | 4.22 | 216 | 206 | 211 | 3.35 | 6.5 |
| patient u | 1:10 | 204 | 192 | 198 | 4.28 | 199 | 189 | 194 | 3.64 | 4 |
| patient p | 1:10 | 59 | 58 | 58.5 | 1.20 | 60 | 58 | 59 | 2.39 | −0.5 |
| smith | 1:10 | 157 | 150 | 153.5 | 3.22 | 155 | 150 | 152.5 | 2.31 | 1 |
| patient o | 1:10 | 63 | 55 | 59 | 9.58 | 63 | 55 | 59 | 9.58 | 0 |
| patient z | 1:30 | 1226 | 1175 | 1200. | 3.00 | 1173 | 1138 | 1155. | 2.14 | 45 |
| patient q | 1:10 | 103 | 97 | 100 | 4.24 | 104 | 98 | 101 | 4.20 | −1 |
| patient w | 1:10 | 204 | 196 | 200 | 2.82 | 200 | 192 | 196 | 2.88 | 4 |
| gormley | 1:05 | 48 | 42 | 45 | 9.42 | 48 | 42 | 45 | 9.42 | 0 |
| patient v | 1:10 | 243 | 213 | 228 | 9.30 | 233 | 208 | 220.5 | 8.01 | 7.5 |
| patient r | 1:10 | 110 | 98 | 104 | 8.15 | 112 | 99 | 105.5 | 8.71 | −1.5 |
| patient y | 1:20 | 963 | 982 | 972.5 | 1.38 | 938 | 964 | 951 | 1.93 | 21.5 |

For the polynomial, the mean C.V. percent is equal to the square root of the sum of the C.V. percent squared divided by N which equals 725.25 divided by 35 equals 35 (to the one half power) which equals 4.55%. Similarly, the mean C.V. percent for the first order regression analysis is 4.65% thereby indicating that slightly better results are obtained from the higher order polynomial regression analysis.

It will be readily appreciated that the foregoing Examples have been given in terms of fibrinogen assays as these assays are the most difficult and most critical to perform. Clearly, the methods of the instant invention are not limited thereto and will be equally applicable to and indeed, more easily employed with the PT and APTT determinations. Thus, the Examples should not be construed as limiting.

Further, one skilled in the art will readily appreciate that numerous alterations and substitutions with regard to the foregoing, for example the employment of different order polynomial regression analysis, the substitution of cubic spline fits, and the like, do not deviate from the spirit and scope of the principles of the instant invention.

What is claimed

1. In a system for monitoring the presence of a coagulation component in a mixture of coagulation reagent and patient sample by measuring component clotting detection time, and employing a sensor for determining increases in optical density and providing a signal in coordination therewith, a method comprising:
   (a) measuring and subsequently storing the values of the signal proportional to the optical property of the mixture at a plurality of times during a predetermined interval after formation of the mixture;
   (b) determining the last stored value of the signal at the end of the predetermined interval;
   (c) scanning all stored signal values starting with the last stored signal value to determine a time T1 when the measured signal is more than or equal to a fraction X times the last stored signal value;
   (d) further scanning the stored signal values starting with the last stored signal value to determine a time T2 when the measured signal is less than or equal to a fraction Y times the last stored signal value, wherein $1 > Y > X > 0$;
   (e) producing a function relating the stored signal values to the plurality of times by performing a curve fitting analysis of the stored signal values for the times bounded by times T1 and T2; and
   (f) determining from the function the time at which the value of the signal is equal to Z times the last stored signal value, wherein $1 > Z > 0$, whereby the component clotting detection time is determined.

2. The method as provided in claim 1 where the stored signal values are normalized by a method selected from the group of following:
   (a) adjusting the lowest stored signal value to zero and reducing all the other stored signal values by an amount equal to the lowest stored signal value, prior to the step of determining the last stored value of the signal; and
   (b) prior to storing the signal values, reducing the measured values by the lowest measured signal value.

3. The method as provided in claim 2 wherein the curve fitting analysis comprises a polynomial regression analysis of the first order.

4. The method as provided in claim 3 wherein the detection time is correlated with a standard curve to obtain the concentration of the coagulant component in the sample.

5. The method as provided in claim 4 wherein the method is employed to a determination selected from the group consisting of fibrinogen, PT, APTT, and factor assays.

6. A method for determining a fibrinogen, PT, APTT, or factor coagulation time by monitoring the optical density of a mixture of patient sample and coagulation reagent with a sensor capable of supplying a continuous signal, comprising the steps of:

(a) measuring and storing the signal values proportional to an optical property of the mixture at a plurality of times during a predetermined time interval during which the coagulation time is to be determined;

(b) normalizing the measured signal values by setting the lowest measured signal value to zero and reducing all other measured signal values by the value of the lowest measured signal value;

(c) determining the value of the signal last measured at the end of the predetermined interval;

(d) scanning the measured values of the signal starting with the last measured signal to determine the time T1 of the first measured signal, the value of which is equal to or more than the fraction X times the last measured signal value and T2 of the first signal, the value of which is less than or equal to the fraction Y times the last measured signal value, wherein $1 > Y > X > 0$;

(e) performing a polynomial regression analysis of order P of the measured values of the signal over a time period bounded by times T1 and T2 to form a function, wherein P is greater than or equal to tow; and (f) determining from the function the time at which the value of the signal is equal to the fraction Z times the last measured value of the signal, wherein $1 > Z > 0$ and whereby fibrinogen, partial thromboplastin or prothrombin coagulation time is determined.

7. The method as provided in claim 6 wherein the value of the last measured signal of the predetermined interval is determined by averaging the last five measured values of the signal.

8. The method as provided in claim 7 further comprising the step of correlating the detection time with a standard curve to obtain the concentration of the coagulant component in the sample.

* * * * *

UNITED STATES PATENT AND TRADEMARK OFFICE
CERTIFICATE OF CORRECTION

PATENT NO. : 4,720,787
DATED : January 19, 1988
INVENTOR(S) : Myatt S. Lipscomb

It is certified that error appears in the above-identified patent and that said Letters Patent is hereby corrected as shown below:

Column 14, line 8, delete "tow" and insert --two--.

Signed and Sealed this

Seventeenth Day of January, 1989

Attest:

DONALD J. QUIGG

*Attesting Officer*    *Commissioner of Patents and Trademarks*